United States Patent [19]
Watanabe et al.

[11] Patent Number: 4,814,540

[45] Date of Patent: Mar. 21, 1989

[54] PROCESS FOR PRODUCING PROPYLENE OLIGOMERS

[75] Inventors: Masami Watanabe; Masahiko Kuramoto, both of Chiba, Japan

[73] Assignee: Idemitsu Kosan Company Limited, Tokyo, Japan

[21] Appl. No.: 121,507

[22] Filed: Nov. 13, 1987

[30] Foreign Application Priority Data

Nov. 13, 1986 [JP] Japan .................. 61-270606
Dec. 25, 1986 [JP] Japan .................. 61-314436

[51] Int. Cl.$^4$ ................................ C07C 2/02
[52] U.S. Cl. .................... 585/523; 585/512; 585/513; 585/520
[58] Field of Search ............... 585/512, 513, 520, 523

[56] References Cited

U.S. PATENT DOCUMENTS

| | | | |
|---|---|---|---|
| 3,969,429 | 7/1976 | Belov et al. | 585/513 |
| 4,252,987 | 2/1981 | Goodall et al. | 585/513 |
| 4,542,199 | 9/1985 | Kaminsky et al. | 502/117 |
| 4,544,762 | 10/1985 | Kaminsky et al. | 585/502 |
| 4,658,078 | 4/1987 | Slaugh et al. | 585/512 |
| 4,665,047 | 5/1987 | Slaugh et al. | 502/117 |

*Primary Examiner*—Curtis R. Davis
*Attorney, Agent, or Firm*—Armstrong, Nikaido, Marmelstein & Kubovcik

[57] ABSTRACT

Disclosed is a process for producing propylene oligomers at high selectivities which comprises oligomerizing propylene in the presence of a catalyst comprising an alkyl substituted cyclopentadienyl compound of zirconium and/or hafnium and a condensation product of organoaluminum compound and water.

16 Claims, No Drawings

PROCESS FOR PRODUCING PROPYLENE OLIGOMERS

BACKGROUND OF THE INVENTION

This invention relates to a process for producing propylene oligomers (The meaning of this "Oligomer" contains "dimer" and "telomer".) used, for example, as starting materials for polymers, base materials for preparing lubricating oils and starting materials for various chemical products. More particularly, it relates to a process for producing propylene oligomers having mainly a polymerization degree of 2-10 and having a vinyl group at terminal of molecule at a high selectivity.

It is known that Ziegler-Natta catalyst is used for production of propylene oligomers in addition to solid catalysts containing alkali metals. Typically, it has been known to polymerize propylene using catalysts comprising combination of nickel compound and aluminum compound or catalysts comprising titanium compound and organoaluminum compound, or sodium-potassium catalysts.

However, products obtained by these processes are mixtures of various components such as polymers having vinyl group at molecular terminal, various internal olefins such as dimers, e.g., 2-methylpentene-2,4-methylpentene-2,2,3-dimethylbutene-2, hexene-2, etc., vinylidene compounds such as dimers, e.g., 2-methylpentene-1,2,3-dimethylbutene-1, etc. Therefore, complicated separating operations are necessary for obtaining industrially useful propylene oligomers having vinyl group at molecular terminal. There is another problem that selectivity per se of the propylene oligomers having vinly group at molecular terminal is low.

SUMMARY OF THE INVENTION

This invention has been made under the above circumstances.

That is, the object of this invention is to provide a process which can produce propylene oligomers having a polymerization degree of mainly 2-10 and having vinyl group at molecular terminal at high selectivities.

As a result of the inventors' intensive researches for attaining this object, it has been found that propylene oligomers which are industrially useful and have vinyl group at molecular terminal can be produced efficiently at a high selectivity by polymerizing propylene in the presence of hydrogen and a catalyst comprising a specific transition metal compound and a specific organometallic compound. This invention has been accomplished based on this finding.

That is, this invention relates to a process for producing propylene oligomers using a catalyst comprising a transition metal compound and an organometallic compound, characterized in that an alkyl substituted cyclopentadienyl compound of zirconium and/or alkyl substituted cyclopentadienyl compound of hafnium is used as the transition metal compound and a condensation product of an organoaluminum compound and water is used at the organometallic compound.

DETAIL DESCRIPTION OF THE INVENTION

Said alkyl substituted cyclopentadienyl compound of zirconium or said alkyl substituted cyclopentadienyl compound of hafnium (which is referred to as merely "cyclopentadienyl compound" hereinafter) can be represented by the following formula [1].

$$(R_5C_5)_m \cdot M \cdot X_{4-m} \quad [1]$$

(wherein R represents an alkyl group of 1-20 carbon atoms, $R_5C_5$ represents a cyclopentadienyl group substituted with an alkyl group (referred to as "alkyl substituted cyclopentadienyl group"), M represents zirconium atom or hafnium atom, X represents hydrogen, and alkyl group of 1-20 carbon atoms or a halogen and m represents a real number of 2-4).

The alkyl group represented by R or X in the above formula [1] has 1-20 carbon atoms and as examples thereof, mention may be made of methyl, ethyl, propyl, isopropyl, butyl, isobutyl, amyl, hexyl, heptyl, octyl, nonyl, capryl, undecyl, lauryl, tridecyl, myristyl, pentadecyl, cetyl, heptadecyl, stearyl, nonadecyl and eicosyl groups.

The halogens represented by X in the formula [1] have no special limitations, but chlorine is preferred. Typical examples of the alkyl substituted cyclopentadienyl compounds represented by the formula [1] are as follows:

[(CH$_3$)$_5$C$_5$]$_2$ZrCl$_2$,      [(CH$_3$)$_5$C$_5$]$_2$HfCl$_2$,
[(C$_2$H$_5$)$_5$C$_5$]$_2$ZrCl$_2$,   [(C$_2$H$_5$)$_5$C$_5$]$_2$HfCl$_2$,
[(C$_3$H$_7$)$_5$C$_5$]$_2$ZrCl$_2$,   [(C$_3$H$_7$)$_5$C$_5$]$_2$HfCl$_2$,
[(CH$_3$)$_5$C$_5$]$_2$ZrHCl,          [(CH$_3$)$_5$C$_5$]$_2$HfHCl,
[(C$_2$H$_5$)$_5$C$_5$]$_2$ZrHCl,      [(C$_2$H$_5$)$_5$C$_5$]$_2$HfHCl,
[(C$_3$H$_7$)$_5$C$_5$]$_2$ZrHCl,      [(C$_3$H$_7$)$_5$C$_5$]$_2$HfHCl,
[(C$_2$H$_5$)(CH$_3$)$_4$C$_5$]$_2$ZrCl$_2$,   [(C$_2$H$_5$)(CH$_3$)$_4$C$_5$]$_2$HfCl$_2$,
[(C$_3$H$_7$)(CH$_3$)$_4$C$_5$]$_2$ZrCl$_2$,   [(C$_3$H$_7$)(CH$_3$)$_4$C$_5$]$_2$HfCl$_2$,
[(C$_4$H$_9$)(CH$_3$)$_4$C$_5$]$_2$ZrCl$_2$,   [(C$_4$H$_9$)(CH$_3$)$_4$C$_5$]$_2$HfCl$_2$,
[(C$_2$H$_5$)(CH$_3$)$_4$C$_5$]$_2$ZrHCl,      [(C$_2$H$_5$)(CH$_3$)$_4$C$_5$]$_2$HfHCl,
[(C$_3$H$_7$)(CH$_3$)$_4$C$_5$]$_2$ZrHCl,      [(C$_3$H$_7$)(CH$_3$)$_4$C$_5$]$_2$HfHCl,
[(C$_4$H$_9$)(CH$_3$)$_4$C$_5$]$_2$ZrHCl,      [(C$_4$H$_9$)(CH$_3$)$_4$C$_5$]$_2$HfHCl$_2$,
[(CH$_3$)$_5$C$_5$]$_2$Zr(CH$_3$)$_2$,          [(CH$_3$)$_5$C$_5$]$_2$Hf(CH$_3$)$_2$,
[(C$_2$H$_5$)(CH$_3$)$_4$C$_5$]$_2$Zr(CH$_3$)$_2$,
[(C$_2$H$_5$)(CH$_3$)$_4$C$_5$]$_2$Hf(CH$_3$)$_2$,

These may be used alone or in combination of two or more.

Among these alkyl substituted cyclopentadienyl compounds, preferred are hafnium compounds.

As the organoaluminum compounds, those represented by the formulas: AlR$^2$$_3$, AlR$^3$$_2$Y and Al$_2$R$^4$$_3$Y$_3$ are widely used. In these formulas, R$^2$, R$^3$ and R$^4$ represent cycloalkyl group, aryl group or alkyl group of 1-10, preferably 1-5 carbon atoms and Y represents hydrogen atom, a halogen atom such as chlorine, bromine or the like or an alkoxy group such as methoxy, ethoxy or the like.

As examples of the organoaluminum compounds represented by the above general formulas, mention may be made of trialkylaluminums such as trimethylaluminum, triethylaluminum, tripropylaluminum, triisopropylaluminum, tributylaluminum, triisobutylaluminum, triamylaluminum, trioctylaluminum, etc. dialkylaluminum monohalides such as diethylaluminum monochloride, diisopropylaluminum monochloride, diisobutylaluminum monochloride, dioctylaluminum monochloride, etc., ehtylaluminum sesquichloride, diethylaluminum hydride, dimethylaluminum ethoxide, diethylaluminum methoxide, etc.

In this invention, above various organoaluminum compounds may be used alone or in combination of two or more.

Of said various organoaluminum compounds which are essential in this invention, trialkylaluminums represented by the general formula: AlR$^5$$_3$ (wherein R$^5$ represents an alkyl group of 1-5 carbon atoms (are preferred and trimethylaluminum, triethylaluminum, etc. are especially preferred.

It is known that an aluminoxane is usually produced by condensation reaction of an organoaluminum compound and water. The water used has no special limitation and may contain some impurities as long as production of the aluminoxane is not inhibited. Further, water of crystallization in hydrous salt may also be used as water.

The aluminoxanes obtained by condensation of said organoaluminum compound and water include, for example, methylaluminoxane, ethylaluminoxane, propylaluminoxane, isopropylaluminoxane, butylaluminoxane, isobutylaluminoxane, amylaluminoxane, etc.

The condensation products of organoaluminum compounds and water have no special limitations in their molecular weight and process for preparation thereof. For example, the organoaluminum compounds and water may be condensed in low polymerization reaction zone or the organoaluminum compound and water may be condensed before feeding them to low polymerization reaction zone. Furthermore, the obtained condensation product may be supported on a solid carrier and used. Further, the condensation product may be combined with other organoaluminum compounds.

The blending ratio of the alkyl substituted cyclopentadienyl compound and the condensation product of the organoaluminum compound and water is preferably such that the atomic ratio, aluminum atom/zirconium atom or hafnium atom is 10-5,000.

According to this invention, propylene oligomers can be produced at a high selectivity by polymerizing propylene in the presence of a catalyst obtained from the alkyl substituted cyclopentadienyl of zirconium of hafnium and the condensation product of the organoaluminum compound and water.

As the propylene, there may be used those obtained by fractional distillation of cracking gas of petroleum or natural gas.

Reaction temperature of the polymerization (oligomerization) reaction of propylene has no special limitation and normally is 0°–100° C., preferably 20°–80° C. This oligomerization reaction may be carried out under optional pressures, for example, a low pressure of lower than 10 kg/cm$^2$G or, if desired, atmospheric pressure.

If the reaction temperature is lower, polymers of high polymerization degree are apt to be produced while if it is higher, those of lower polymerization degree such as dimers, trimers, etc. are produced. Thus, reaction temperature may be optionally determined depending on the desired products. However, when reaction temperature is higher than 100° C., activity of catalyst may be reduced.

Solvents can be used in the oligomerization reaction of propylene.

As the solvents, mention may be made of, for example, aromatic hydrocarbons such as benzene, toluene, xylene, ethylbenzene, cumene, mesitylene, naphthalene, tetralin, butylbenzene, p-cymene, cyclohexylbenzene, diethylbenzene, pentylbenzene, dipentylbenzene, dodecylbenzene, biphenyl, etc.; aliphatic hydrocarbons such as 2-methylbutane, hexane, 2-methylpentane, 2,2-dimethylbutane, 2,3-dimethylbutane, heptane, octane, 2,2,3-trimethylpentane, isooctane, nonane, 2,2,5-trimethylhexane, decane, dodecane, etc.; and cyclohexane, decalin, petroleum ether, petroleum benzine, petroleum naphtha, ligroin, industrial gasoline, kerosene, etc.

The polymerization may be carried out by any of solution polymerization method, bulk polymerization method, vapor phase polymerization method and the like, but solution polymerization method is preferred from the viewpoint of catalytic activity.

According to the process of this invention, a mixture comprising mainly oligomers having a vinyl group at molecular terminal and represented by the general formula:

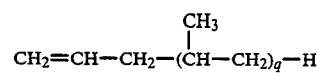

(wherein q indicates a real number of 1–9) can be obtained under simple and moderate conditions and at a high selectivity.

According to the inventors' further research, it has been found that when hydrogen is allowed to exist in the oligomerization reaction of propylene, polymerization activity is enhanced and surprisingly, even if hydrogen is present in the reaction, hydrogenation reaction of propylene does not occur and conversion rate of propylene can be increased without causing reduction of selectivity of propylene.

As said hydrogen, there may be used hydrogen obtained by modification of water gas, gasification of petroleums, complete gasification of coal, modification of natural gas, etc.

Amount of hydrogen used is optional, but normally is 1–100 mol%, preferably 5–50 mol% based on starting propylene.

According to the inventors' further research, it has been found that when a reaction product of said alkyl substituted cyclopentadienyl compound of zirconium and/or said alkyl substituted cyclopentadienyl compound of hafnium with an electron donating compound is used in the oligomerization reaction of propylene in the presence of hydrogen, conversion rate of propylene can be enhanced without causing reduction of selectivity of propylene as compared with when oligomerization is effected in the presence of a catalyst obtained from the alkyl substituted cyclopentadienyl compound and a condensation product of organoaluminum compound and water.

The electron donating compound includes, for example, organic compounds containing oxygen, nitrogen, phosphorus or sulfur or olefins. As examples thereof, mention may be made of amines, amides, ketones, nitriles, phosphines, phosphorylamide, esters, ethers, thioethers, thioesters, acid anhydrides, acid amides, acid halides, aldehydes, organic acids, etc.

As more specific examples, mention may be made of organic acids such as aromatic carboxylic acids, e.g., benzoic acid, p-oxybenzoic acid, etc.; acid anhydrides such as succinic anhydride, benzoic anhydride, p-toluylic anhydride, etc.; ketones of 3–15 carbon atoms such as acetone, methyl ethyl ketone, methyl isobutyl ketone, acetophenone, benzophenone, benzoquinone, etc.; aldehydes of 2–15 carbon atoms such as acetoaldehyde, propionaldehyde, octylaldehyde, benzaldehyde, tolualdehyde, naphthoaldehyde, etc.; esters of 2–18 carbon atoms such as methyl formate, methyl acetate, ethyl acetate, vinyl acetate, propyl acetate, octyl acetate, cyclohexyl acetate, ethyl propionate, ethyl butyrate, ethyl valerate, methyl chloroacetate, ethyl dichloroacetate, methyl methacrylate, ethyl crotonate, ethyl pivalate, dimethyl maleate, ethyl cyclohexanecarboxylate, methyl benzoate, ethyl benzoate, propyl benzoate, butyl benzoate, octyl benzoate, cyclohexyl benzoate, phenyl benzoate, benzyl benzoate, methyl methoxybenzoate, ethyl methoxybenzoate, methyl toluylate, amyl toluylate, ethyl ethylbenzoate, methyl anisate, ethyl anisate, ethyl ethoxybenzoate, ethyl p-butoxybenzoate, ethyl o-chlorobenzoate, ethyl naphthoate, γ-butyrolactone, δ-valerolactone, cumalin, phthalide, ethylene carbonate, etc.; acid halides of 2–15 carbon atoms such as acetyl chloride, benzyl chloride, toluylic acid chloride, anisic acid chloride, etc.; ethers of 2–20 carbon atoms such as methyl ether, ethyl ether, isopropyl ether, n-butyl ether, amyl ether, tetrahydrofuran, anisole, diphenyl ether, ethylene glycol butyl ether, etc.; acid amides such as acetic amide, benzoic acid amide, toluylic acid amide, etc.; amines such as tributylamine, N,N'-dimethylpiperazine, tribenzylamine, aniline, pyridine, picoline, tetramethylethylenediamine, etc.; nitrules such as acetonitrile, benzonitrile, tolunitrile, etc.; teteramethyl urea, nitrobenzene, lithium butyrate, piperidine, toluidine, etc.

The phosphorus compounds include, for example, phosphoric acid or phosphorous acid esters and phosphines represented by the general formula: $PO(OR^1)_3$ or $PR^1_3$ (wherein $R^1$ represents an aliphatic hydrocarbon group, unsaturated aliphatic hydrocarbon grup, aromatic hydrocarbon group, a halogen or hydrogen). As examples thereof, mention may be made of phosphoric acid esters or halides such as trimethyl phosphate, triethyl phosphate, tributyl phosphate, triphenyl phosphate, diphenylphosphoric acid chloride, phenylphosphoric acid dichloride, etc.; phosphorous acid esters or halides such as methyl phosphite, ethyl phosphite, butyl phosphite, triphenyl phosphite, tri-2,4-di-tertiary-butylphenyl phosphite, diphenylphosphorous acid chloride, phenylphosphorous acid dichloride, etc.; phosphines such as triethylphosphine, tributylphosphine, diphenylchlorophosphine, phenyldichlorophosphine, etc.

Preferable electron donating compounds are esters, ethers, ketones, phosphorus compounds, organic compounds containing nitrogen such as amines.

More preferable electron donating compounds are at least one selected from the group consisting of aromatic carboxylic acid esters, aromatic amines and heterocyclic amines.

Further preferable electron donating compounds are at least one selected from the gorup consisting of lower alkyl esters of benzoic acid, lower alkyl esters of lower alkoxybenzoic acid, aniline which may have lower alkyl group as substituent in benzene ring and piperidine.

Especially preferred electron donating compounds are selected from ethyl benzoate, ethyl methoxybenzoate, toluidine and piperidine.

Further preferred are alkyl esters of aliphatic carboxylic acids such as methyl acetate, ethyl acetate, etc. and alkyl ($C_1$-$C_4$) esters of aromatic carboxylic acids such as benzoic acid, p-methoxybenzoic acid, p-ethoxybenzoic acid, toluylic acid, etc. Furthermore, aromatic ketones such as benzoquinone, etc., aromatic carboxylic acid anhydrides such as benzoic anhydride, etc., ethers such as ethylene glycol butyl ether, etc., heterocyclic amines such as piperdine, etc., aromatic amines which may be substituted with lower alkyl group, etc. are also preferred.

Said alkyl substituted cyclopentadienyl compound and said electron donating compound react with each other when mixed to yield a reaction product. This reaction product is at least a coordination compound wherein the electron donating compound coordinates with the alkyl substituted cyclopentadienyl compound.

The ratio (b)/(a) of the alkyl substituted cyclopentadienyl compound (a) and the electron donating compound (b) is usually 0.1–10, preferably 0.5–2 in molar ratio.

The oligomers obtained by the process of this invention are useful as starting materials for homopolymers (for example, 4-methylpentene-1), as comonomers for straight chain low-density polyethylenes or starting materials for other polymers and as starting materials for lubricating oil bases and starting materials for chemical syntheses.

According to the process of this invention, mixtures of propylene oligomers having a polymerization degree of mainly 2–10 and having a vinyl group at molecular terminal can be produced at a high selectivity.

Therefore, this invention can provide a novel process for production of propylene oligomers by which industrially highly useful propylene oligomers having a vinyl group at molecular terminal can be efficiently produced.

This invention is explained in more detail by the following examples and comparative examples.

EXAMPLE 1

(1) Preparation of Aluminum Catalyst Component 200 ml of toluene was put in a reactor and thereto were further added 47.4 ml (492 mmols) of trimethylaluminum and 35.5 g (142 mmols) of cupric sulfate pentahydrate ($CuSO_4.5H_2O$). Reaction was carried out in argon stream at 20° C. for 24 hours.

The copper sulfate was removed by filtration and toluene was distilled off to obtain 12.4 g of methylaluminoxane.

This methylaluminoxane had a molecular weight of 721 measured by cryoscopic method in benzene.

(2) Polymerization (Oligomerization) of Propylene

In an autoclave of 1 liter in internal volume were successively added 400 ml of toluene, 6 mmols (in terms of aluminum equivalent) of methylaluminoxane obtained in the above (1) 0.01 mmol of bis(pentamethylcyclopentadienyl)zirconium dichloride and temperature was elevated to 50° C.

Then, propylene was continuously introduced into the autocalve and reaction was effected at 50° C. for 4 hours with keeping propylene partial pressure at 8 kg/cm²G.

After completion of the reaction, the product was subjected to removal of ash with 150 ml of 3N hydrochloric acid to obtain 30.3 g of a mixture of propylene oligomers.

Thus obtained mixture was analyzed to find that it contained 4.7 g of dimer, 1.8 g of trimer and 23.8 g of oligomers of tetramer and higher oligomers and it had an average polymerization degree of 4.6.

The mixture were also subjected to infrared absorption spectrum analysis and $^1HNMR$ (270MHz) analysis to find that content of propylene oligomers having vinyl group at molecular terminal (absorption peaks; 1640 $cm^{-1}$, 994 $cm^{-1}$, 912 $cm^{-1}$) was 92% and that of propylene oligomers having vinylidene group at molecular terminal (absorption peak; 884 $cm^{-1}$) was 8%.

Furthermore, analysis of the dimer showed that 4-methylpentene-1 was a main component and selectivity thereof was 98%.

The results are shown in Table 1.

EXAMPLES 2-15

Example 1 was repeated except that catalyst components and polymerization temperature as shown in Table 1 were employed.
The results are shown in Table 1.

EXAMPLE 16

A propylene oligomers were produced in the same manner as in Example 1 except that bis(pentamethylcyclopentadienyl)hafnium dichloride was used in place of bis(pentamethylcyclopentadienyl)zirconium dichloride and hexane was used as polymerization solvent in place of toluene.
The results are shown in Table 1.

EXAMPLE 17

In an autoclave of 1 liter in internal volume were charged 400 ml of toluene and 5 mmols of trimethylaluminum at room temperature, followed by adding 3.9 mmols of water and reaction was effected for 10 minutes. Then, thereto was added 0.01 mmols of bis(pentamethylcyclopentadienyl)hafnium dichloride and the temperature was elevated to 50° C. Thereafter, propylene was continuously introduced into the autocalve to carry out reaction at 50° C. for 4 hours with keeping propylene partial pressure at 8 kg/cm²G to obtain propylene oligomers. Treatments after the reaction were effected in the same manner as in Example 1 (2).
The results are shown in Table 1.

EXAMPLE 18

Propylene oligomers were obtained in the same manner as in Example 1 except that bis(pentamethylcyclopentadienyl)hafnium dichloride was used in place of bis(pentamethylcyclopentadienyl)zirconium dichloride and a mixture of 6 mmols (in terms of aluminum equivalent) of methylaluminoxane and 6 mmols (in terms of aluminum equivalent) of trimethylaluminum was used as the organoaluminum compound used at polymerization.
The results are shown in Table 1.

COMPARATIVE EXAMPLE 1

Propylene oligomers were produced in the same manner as in Example 1 except that bis(cyclopentadienyl)zirconium dichloride was used in place of bis(pentamethylcyclopentadienyl)zirconium dichloride.
The results are shown in Table 1.

COMPARATIVE EXAMPLE 2

Propylene oligomers were produced in the same manner as in Comparative Example 1 except that bis(cyclopentadienyl)hafnium dichloride was used in place of bis(cyclopentadienyl)zirconium dichloride.
The results are shown in Table 1.

COMPARATIVE EXAMPLE 3

Propylene oligomers were produced in the same manner as in Comparative Example 1 except that bis(cyclopentadienyl)titanium dichloride was used in place of bis(cyclopentadienyl)zirconium dichloride.
The results are shown in Table 1.

In these comparative examples, polymerization reaction took place preferentially to oligomerization reaction and product were all high polymers which predominantly had vinylidene group as terminal unsaturated group.

TABLE 1

| | Transition metal compound | mmol | Organometallic compound | mmol *4 | Temp. (°C.) | Time (Hr) | Total yield (g) |
|---|---|---|---|---|---|---|---|
| Example 1 | $[(CH_3)_5C_5]_2ZrCl_2$ | 0.01 | Methylaluminoxane | 6 | 50 | 4 | 30.3 |
| Example 2 | $[(CH_3)_5C_5]_2ZrCl_2$ | 0.06 | Methylaluminoxane | 6 | 50 | 4 | 91.0 |
| Example 3 | $[(CH_3)_5C_5]_2ZrCl_2$ | 0.01 | Methylaluminoxane | 6 | 20 | 4 | 36.9 |
| Example 4 | $[(CH_3)_5C_5]_2ZrCl_2$ | 0.01 | Methylaluminoxane | 6 | 80 | 4 | 16.6 |
| Example 5 | $[(CH_3)_5C_5]_2ZrHCl$ | 0.01 | Methylaluminoxane | 6 | 50 | 4 | 13.8 |
| Example 6 | $[(CH_3)_5C_5]_2ZrHCl$ | 0.01 | Methylaluminoxane | 6 | 80 | 4 | 7.5 |
| Example 7 | $[(CH_3)_5C_5]_2HfCl_2$ | 0.01 | Methylaluminoxane | 6 | 20 | 4 | 78.8 |
| Example 8 | $[(CH_3)_5C_5]_2HfCl_2$ | 0.06 | Methylaluminoxane | 6 | 50 | 4 | 148.2 |
| Example 9 | $[(CH_3)_5C_5]_2HfCl_2$ | 0.01 | Methylaluminoxane | 6 | 50 | 4 | 61.2 |
| Example 10 | $[(CH_3)_5C_5]_2HfCl_2$ | 0.01 | Methylaluminoxane | 12 | 50 | 4 | 176.6 |
| Example 11 | $[(CH_3)_5C_5]_2HfCl_2$ | 0.01 | Methylaluminoxane | 6 | 80 | 4 | 17.1 |
| Example 12 | $[(CH_3)_5C_5]_2HfHCl$ | 0.01 | Methylaluminoxane | 6 | 50 | 4 | 26.7 |
| Example 13 | $[(CH_3)_5C_5]_2HfHCl$ | 0.01 | Methylaluminoxane | 6 | 80 | 4 | 14.6 |
| Example 14 | $[(CH_3)_5C_5]_2HfCl_3$ | 0.01 | Methylaluminoxane | 6 | 50 | 1 | 56.0 |
| Example 15 | $[(CH_3)_5C_5]_2HfCl_2$ | 0.01 | Methylaluminoxane | 6 | 80 | 4 | 73.4 |
| Example 16 *3 | $[(CH_3)_5C_5]_2HfCl_2$ | 0.01 | Methylaluminoxane | 6 | 50 | 4 | 85.1 |
| Example 17 | $[(CH_3)_5C_5]_2HfCl_2$ | 0.01 | Trimethyl aluminium $H_2O$ | 6 3.9 | 50 | 4 | 14.0 |
| Example 18 | $[(CH_3)_5C_5]_2HfCl_2$ | 0.01 | Methylaluminoxane $Al(CH_3)_3$ | 6 6 | 50 | 4 | 141.9 |
| Comparative Example 1 | $(C_5H_5)_2ZrCl_2$ | 0.01 | Methylaluminoxane | 6 | 50 | 4 | 90.1 |
| Comparative Example 2 | $(C_5H_5)_2HfCl_2$ | 0.01 | Methylaluminoxane | 6 | 50 | 4 | 21.3 |
| Comparative Example 3 | $(C_5H_5)_2TiCl_2$ | 0.01 | Methylaluminoxane | 6 | 50 | 4 | 0.5 |

| | Dimer (g) | Trimer (g) | Selectivity (%) (*1/*2) | Selectivity (%) (4-MP-1) | Average polymerization degree |
|---|---|---|---|---|---|
| Example 1 | 4.7 | 1.8 | 92/8 | 98 | 4.6 |
| Example 2 | 9.3 | 10.0 | 92/8 | 98 | 4.4 |
| Example 3 | 0 | 1.0 | 92/8 | — | 18.1 |
| Example 4 | 11.6 | 1.9 | 90/10 | 90 | 2.5 |
| Example 5 | 2.2 | 0.5 | 92/8 | 98 | 4.8 |
| Example 6 | 6.6 | Trace | 90/10 | 90 | 2.3 |
| Example 7 | 4.8 | 9.0 | 97/3 | 100 | 7.1 |

TABLE 1-continued

| | | | | | |
|---|---|---|---|---|---|
| Example 8 | 54.1 | 42.0 | 98/2 | 100 | 3.1 |
| Example 9 | 27.0 | 13.9 | 98/2 | 100 | 3.3 |
| Example 10 | 64.0 | 39.5 | 98/2 | 100 | 3.5 |
| Example 11 | 15.4 | 1.4 | 95/5 | 96 | 2.2 |
| Example 12 | 12.9 | 6.8 | 98/2 | 100 | 3.3 |
| Example 13 | 13.3 | 1.2 | 95/5 | 96 | 2.2 |
| Example 14 | 25.3 | 17.1 | 98/2 | 100 | 2.9 |
| Example 15 | 28.6 | 25.4 | 98/2 | 100 | 2.2 |
| Example 16 *3 | 25.8 | 27.9 | 98/2 | 100 | 3.3 |
| Example 17 | 6.9 | 4.0 | 98/2 | 100 | 2.2 |
| Example 18 | 44.2 | 34.8 | 98/2 | 100 | 2.9 |
| Comparative Example 1 | 0.0 | 0.0 | — | — | 41.9 |
| Comparative Example 2 | 0.0 | 0.0 | — | — | 233.8 |
| Comparative Example 3 | 0.0 | 0.0 | — | — | 1355 |

*1: Propylene oligomer having vinyl group at molecular terminal
*2: Propylene oligomer having vinylidene group at molecular terminal
*3: Hexane was used as a solvent
*4: Millimol in terms of aluminum equivalent 4-MP-1:4-Methyl-pentene-1

EXAMPLE 19

Example 1 was repeated except that bis(pentamethylcyclopentadienyl)hafnium dichloride was used in place of bis(pentamethylcyclopentadienyl)zirconium dichloride and hidrogen was introduced into the autoclave at 1 kg/cm$^2$G and furthermore, propylene was continuously introduced therein. As a result, there was obtained 181.7 g of a mixture of propylene oligomers.

Thus obtained mixture was analyzed to find that it contained 64.7 g of dimer, 58.7 g of trimer and 58.3 g of tetramer and higher oligomers and it had an average polymerization degree of 3.1.

Further, the mixture was subjected to infrared absorption spectrum analysis and $^1$HNMR (270 MH$_z$) to find that content of propylene oligomers having vinyl group at molecular terminal (absorption peaks; 1640 cm$^{-1}$, 994 cm$^{-1}$, 912 cm$^{-1}$) and that of propylene oligomers having vinylidene group at molecular terminal (absorption peak; 884 cm$^{-1}$) was 2%.

Further, the dimer was analyzed to find that main component was 4-methyl-pentene-1 and selectivity thereof was 99%.

The results are shown in Table 2.

EXAMPLE 20

Example 19 was repeated except that amount of toluene used as solvent was 200 ml and amount of bis(pentamethylcyclopentadienyl)hafnium dichloride was 0.005 mmols and polymerization time was 8 hours.

The results are shown in Table 2.

EXAMPLE 21

Example 19 was repeated except that amount of toluene as solvent was 200 ml, amount of bis(pentamethylcyclopentadienyl) hafnium dichloride was 0.005 mmol, a mixture of 6 mmols (in terms of aluminum equivalent) of methylaluminoxane and was used in place of methylaluminoxane and polymerization time was 12 hours.

The results are shown in Table 2.

EXAMLES 22–26 and 28

Example 19 was repeated except that hydrogen partial pressure and polymerization temperature and time as shown in Table 2 were employed.

The results are shown in Table 2.

EXAMPLE 27

Example 19 was repeated except that hexane was used in place of toluene.

The results are shown in Table 2.

EXAMPLE 29

Example 19 was repeated except that bis(pentamethylcyclopentadienyl)zirconium dichloride was used in place of bis(pentamethylcyclopentadienyl)hafnium dichloride.

The results are shown in Table 2.

COMPARATIVE EXAMPLE 4

Propylene oligmers were obtained in the same manner as in Example 19 except that hydrogen was not introduced.

The results are shown in table 2.

In this comparative example, selectivity of oligomers having vinyl group at molecular terminal was similar to that in Example 19, but conversion rate was low and so total yield was very low.

COMPARATIVE EXAMPLE 5

Propylene oligomers were produced in the same manner as in Example 29 except that hydrogen was not introduced.

The results are shown in Table 2.

In this comparative example, selectivity of oligomers having vinyl group at molecular terminal was similar to that in Example 29, but conversion rate was low and hence total yield was low.

COMPARATIVE EXAMPLE 6

Example 19 was repeated except that bis(cyclopentadienyl)hafnium dichloride was used in place of bis(pentamethylcyclopentadienyl)hafnium dichloride.

The results are shown in Table 2.

In this comparative example, propylene oligomers were not obtained and besides infrared absorption spectrum analysis of resulting polymers showed that peaks based on terminal vinylidene group were predominant.

EXAMPLE 30

Example 1 was repeated except that bis(tetramethyl-n-butyl)hafnium dichloride was used in place of bis(pentamethylcyclopentadienyl)zirconium dichloride, hydrogen was introduced into the autoclave at 1 kg/cm²G, reaction temperature was 55° C. and reaction time was 2 hrs.

The result are shown in Table 2.

EXAMPLE 31

Example 30 was repeated except that bis(tetramethyethyl)hafnium dichloride was used in place of bis(tetramethyl-n-butyl)hafnium dichloride.

The result are shown in Table 2.

EXAMPLE 32

Example 30 was repeated except that bis(teteramethyl-n-butyl)zirconium dichloride was used in place of bis(tetramethyl-n-butyl)hafnium dichloride, hydrogen was introduced into the autoclave at 3 kg/cm²G and propylene was introduced into the autoclave at 6 kg/cm²G.

The result are shown in Table 2.

(2) Preparation of Coordination Compound of Transition Metal Compound and Electron Donating Compound A coordination compound was prepared by adding equimolar amounts of bis(pentamethylcyclopentadienyl)hafnium dichloride and benzoic acid to toluene and diluting the mixture.

(3) Polymerization (Oligomerization) of Propylene

Into an autoclave of 1 liter in internal volume were introduced 400 ml of toluene, 6 mmols (in terms of aluminum equivalent) of aluminoxane obtained in the above (1) and 0.01 mmol (in terms of hafnium atom) of coordination compound obtained in the above (2) in this order and the temperature was elevated to 55 C.

Then, hydrogen was introduced into the autoclave at 3 kg/cm²G and further, propylene was continuously introduced to carry out reaction at 55° C. for 8 hours

TABLE 2

| | Transition metal compound | mmol | Organometallic compound | mmol *3 | Propylene partial pressure (kg/cm² G) | Hydrogen partial pressure (kg/cm² G) |
|---|---|---|---|---|---|---|
| Example 19 | $[(CH_3)_5C_5]_2HfCl_2$ | 0.01 | Methylaluminoxane | 6 | 8 | 1 |
| Example 20 | $[(CH_3)_5C_5]_2HfCl_2$ | 0.005 | Methylaluminoxane | 6 | 8 | 1 |
| Example 21 | $[(CH_3)_5C_5]_2HfCl_2$ | 0.005 | Methylaluminoxane Trimethylaluminum | 6 6 | 8 | 1 |
| Example 22 | $[(CH_3)_5C_5]_2HfCl_2$ | 0.01 | Methylaluminoxane | 6 | 7 | 2 |
| Example 23 | $[(CH_3)_5C_5]_2HfCl_2$ | 0.01 | Methylaluminoxane | 6 | 6 | 3 |
| Example 24 | $[(CH_3)_5C_5]_2HfCl_2$ | 0.01 | Methylaluminoxane | 6 | 5 | 4 |
| Example 25 | $[(CH_3)_5C_5]_2HfCl_2$ | 0.01 | Methylaluminoxane | 6 | 8 | 1 |
| Example 26 | $[(CH_3)_5C_5]_2HfCl_2$ | 0.01 | Methylaluminoxane | 6 | 1 | 8 |
| Example 27 | $[(CH_3)_5C_5]_2HfCl_2$ | 0.01 | Methylaluminoxane | 6 | 8 | 1 |
| Example 28 | $[(CH_3)_5C_5]_2HfCl_2$ | 0.01 | Methylaluminoxane | 6 | 8 | 1 |
| Example 29 | $[(CH_3)_5C_5]_2ZrCl_2$ | 0.01 | Methylaluminoxane | 6 | 8 | 1 |
| Example 30 | $[(n-C_4H_9)(CH_3)_4]_2HfCl_2$ | 0.01 | Methylaluminoxane | 6 | 8 | 1 |
| Example 31 | $[(C_2H_5)(CH_3)_4]_2HfCl_2$ | 0.01 | Methylaluminoxane | 6 | 8 | 1 |
| Example 32 | $[(n-C_4H_9)(CH_3)_4]_2HfCl_2$ | 0.01 | Methylaluminoxane | 6 | 6 | 3 |
| Comparative Example 4 | $[(CH_3)_5C_5]_2HfCl_2$ | 0.01 | Methylaluminoxane | 6 | 8 | 0 |
| Comparative Example 5 | $[(CH_3)_5C_5]_2ZrCl_2$ | 0.01 | Methylaluminoxane | 6 | 8 | 0 |
| Comparative Example 6 | $(C_5H_5)_2HfCl_2$ | 0.01 | Methylaluminoxane | 6 | 8 | 1 |

| | Temp. (°C.) | Time (Hr) | Total yield (g) | Dimer (g) | Trimer (g) | Selectivity (%) (*1/*2) | Selectivity (%) (4-MP-1)*4 |
|---|---|---|---|---|---|---|---|
| Example 19 | 50 | 4 | 181.7 | 64.7 | 58.7 | 98/2 | 99 |
| Example 20 | 50 | 8 | 314.0 | 76.4 | 70.2 | 98/2 | 99 |
| Example 21 | 50 | 12 | 329.0 | 81.4 | 80.8 | 98/2 | 99 |
| Example 22 | 50 | 1 | 151.3 | 47.3 | 41.0 | 98/2 | 99 |
| Example 23 | 50 | 1 | 141.2 | 42.5 | 36.3 | 98/2 | 99 |
| Example 24 | 50 | 1 | 136.3 | 44.1 | 37.9 | 98/2 | 98 |
| Example 25 | 50 | 1 | 88.8 | 27.8 | 27.3 | 98/2 | 99 |
| Example 26 | 50 | 4 | 118.6 | 45.9 | 38.9 | 98/2 | 99 |
| Example 27 | 50 | 4 | 69.5 | 18.2 | 19.3 | 98/2 | 99 |
| Example 28 | 80 | 8 | 94.9 | 57.1 | 17.8 | 95/5 | 95 |
| Example 29 | 50 | 4 | 368.6 | 20.1 | 33.6 | 92/8 | 97 |
| Example 30 | 55 | 2 | 128 | 51.2 | 30.7 | 98/2 | 99 |
| Example 31 | 55 | 2 | 156 | 59.3 | 40.6 | 98/2 | 99 |
| Example 32 | 55 | 2 | 91 | 10.0 | 10.0 | 98/2 | 96 |
| Comparative Example 4 | 50 | 4 | 61.2 | 27.0 | 13.9 | 98/2 | 100 |
| Comparative Example 5 | 50 | 4 | 91.0 | 9.3 | 10.0 | 92/8 | 98 |
| Comparative Example 6 | 50 | 4 | 93.2 | 0 | 0 | — | — |

*1: Propylene oligomer having vinyl group at molecular terminal
*2: Propylene oligomer having vinylidene group at molecular terminal
*3: Millimol in terms of aluminum equivalent
*4: 4-Methyl-pentene-1

EXAMPLE 33

(1) Preparation of Aluminum Catalyst Component

Methylaluminoxane was prepared in the same manner as in Example 1 (1).

with keeping the propylene partial pressure at 6 kg/cm²G.

After completion of the reaction, the product was subjected to removal of ash with 150 ml of 3N hydrochloric acid to obtain 324.1 g of a mixture of propylene oligomers.

Analysis of thus obtained mixture of propylene oligomers showed that it contained 76.5 g of dimer, 67.4 g of trimer and 180.2 g of tetramer and the higher oligomers and average polymerization degree was 3.5.

The mixture was further subjected to infrared absorption spectrum analysis and $^1$HNMR (270 MHz) analysis to find that content of propylene oligomers having vinyl group at molecular terminal (absorption peaks; 1640 cm$^{-1}$, 994 cm$^{-1}$, 912 cm$^{-1}$) was 92% and that of propylene oligomers having vinylidene group at molecular terminal (absorption peak; 884 cm$^{-1}$) was 2%.

Furthermore, analysis of the dimer showed that 4-methylpentene-1 was a main component and selectivity thereof was 99%.

The results are shown in Table 3.

EXAMPLES 34–36

Example 33 was repeated except that compounds as shown in table 3 were used as electron donating compounds.

The results are shown in Table 3.

COMPARATIVE EXAMPLE 7

Example 33 was repeated except that electron donating compound was not used.

The results are shown in Table 3.

TABLE 3

| | Electron donating | | Total Yield (g) | Yield of dimer (g) | Selectivity *1/*2 (%) | Selectivity *4 (%) |
|---|---|---|---|---|---|---|
| | Kind | Amount (mM) | | | | |
| Example 33 | Ethyl benzoate | 0.01 | 324.1 | 76.5 | 98/2 | 99.0 |
| Example 34 | Ethyl methoxybenzoate | 0.01 | 232.7 | 76.2 | 98/2 | 99.0 |
| Example 35 | Piperidine | 0.01 | 252.6 | 65.6 | 98/2 | 99.0 |
| Example 36 | Toluidine | 0.01 | 262.3 | 72.8 | 98/2 | 99.1 |
| Comparative Example 7 | — | — | 176.7 | 57.2 | 98/2 | 98.9 |

What is claimed is:

1. A process for producing propylene oligomers using a catalyst comprising a transition metal compound and an organometallic compound which comprises oligomerizing propylene in the presence of a catalyst comprising a cyclopentadienyl compound represented by the formula (1):

$$(R_5C_5)_m \cdot M \cdot X_{4-m} \quad (1)$$

wherein R represents an alkyl group of 1–20 carbon atoms, $R_5C_5$ represents an alkyl substituted cyclopentadienyl group, M represents a zirconium atom or a hafnium atom, X represents a hydrogen atom, an alkyl group of 1–20 carbon atoms or a halogen atom and m represents a real number of 2–4; and a condensation product of an organoaluminum compound and water as an organometallic compound.

2. A process for producing propylene oligomers using a catalyst comprising a transition metal compound and an organometallic compound which comprises oligomerizing propylene in the presence of a catalyst comprising a coordination compound obtained by reacting a cyclopentadienyl compound represented by the formula (1):

$$(R_5C_5)_m \cdot M \cdot X_{4-m} \quad (1)$$

wherein R represents an alkyl group of 1–20 carbon atoms, $R_5C_5$ represents an alkyl substituted cyclopentadienyl group, M represents a zirconium atom or a hafnium atom, X represents a hydrogen atom, an alkyl group of 1–20 carbon atoms or a halogen atom and m represents a real number of 2–4, with an electron donating compound having at least one atom selected from the group consisting of oxygen and nitrogen; and a condensation product of an organoaluminum compound and water as an organometallic compound.

3. A process according to claim 1 wherein the organoaluminum compound is a trialkylaluminum of 1–5 carbon atoms.

4. A process according to claim 1 wherein the organoaluminum compound is at least one compound selected from the group consisting of methylaluminum and triethylaluminum.

5. A process according to claim 2 wherein the electron donating compound is an ester or an organic compound containing nitrogen.

6. A process according to claim 2 wherein the electron donating compound is at least one compound selected from the group consisting of aromatic esters, aromatic amines and heterocyclic amines.

7. A process according to claim 2 wherein the electron donating compound is at least one compound selected from the group consisting of lower alkyl esters of benzoic acid, lower alkyl esters of lower alkoxybenzoic acids, anilines which may have lower alkyl group on benzene ring as a substituent and piperidine.

8. A process according to claim 2 wherein the electron donating compound is a compound selected from the group consisting of ethyl benzoate, ethyl methoxybenzoate, toluidine and piperidine.

9. A process according to claim 1 wherein the blending ratio of the alkyl substituted cyclopentadienyl compound and the condensation product of the organoaluminum compound and water when they are reacted is 10–5,000 in terms of atomic ratio aluminum atom/zirconium atom or hafnium atom.

10. A process according to claim 2 wherein ratio (b)/(a) of the alkyl substituted cyclopentadienyl compound (a) and the electron donating compound (b) is 0.1–10 in molar ratio.

11. A process according to claim 2 wherein the blending ratio of the coordination compound obtained by reaction of the alkyl substituted cyclopentadienyl compound and the electron donating compound and the condensation product of the organoaluminum compound and water is 10–5,000 in terms of atomic ratio of aluminum atom and zirconium or hafnium atom (Al/Zr or Hf).

12. A process according to claim 1 wherein the oligomerization reaction of propylene is carried out at a reaction temperature of 0°–100° C. and a reaction pressure of 10 kg/cm$^2$G or less.

13. A process according to claim 1 wherein the oligomerization reaction of propylene is carried out in a solvent.

14. A process according to claim 1 wherein the propylene oligomer is a mixture of propylene oligomers having vinyl group at molecular terminal which are represented by the formula:

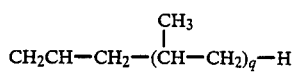

wherein q represents a real number of 1-9.

15. A process for producing propylene oligomers according to claim 1 wherein the propylene is oligomerized reaction proceeds in the presence of hydrogen.

16. A process for producing propylene oligomers according to claim 2 wherein the propylene is oligomerized in the presence of hydrogen.

* * * * *